United States Patent [19]

Suzuki et al.

[11] 4,036,780

[45] July 19, 1977

[54] CATALYST FOR THE PREPARATION OF MALEIC ANHYDRIDE

[75] Inventors: Hideo Suzuki; Takahisa Sato; Tatsuo Kubota; Shigemi Osaka; Shigeru Komatsu, all of Himeji, Japan

[73] Assignee: Nippon Shokubai Kagaku Kogyo Co., Ltd., Japan

[21] Appl. No.: 636,746

[22] Filed: Dec. 1, 1975

[30] Foreign Application Priority Data

Dec. 2, 1974 Japan .................. 49-136995

[51] Int. Cl.$^2$ .................. B01J 27/14; C07D 307/60
[52] U.S. Cl. .................. 252/437; 252/435; 260/346.8 M
[58] Field of Search .................. 252/435, 437

[56] References Cited

U.S. PATENT DOCUMENTS

| | | | |
|---|---|---|---|
| 2,967,185 | 1/1961 | Becker et al. | 252/437 X |
| 3,156,706 | 11/1964 | Kerr | 252/437 X |
| 3,211,671 | 10/1965 | Egbert | 252/435 X |
| 3,226,337 | 12/1965 | Riemenschneider et al. | 252/435 |
| 3,255,211 | 6/1966 | Kerr | 252/435 X |
| 3,288,721 | 11/1966 | Kerr | 252/435 |
| 3,535,346 | 10/1970 | Sudo et al. | 252/437 X |
| 3,917,655 | 11/1975 | Di Cio et al. | 252/435 X |

FOREIGN PATENT DOCUMENTS 1,322,127 12/1963 France .................. 252/435

Primary Examiner—Patrick P. Garvin
Assistant Examiner—William G. Wright
Attorney, Agent, or Firm—Cushman, Darby & Cushman

[57] ABSTRACT

A catalyst for the preparation of maleic anhydride by vapor phase catalytic oxidation of benzene with a molecular oxygen containing gas comprising a porous inert support of an alkali metal content, calculated as oxide, of at most 0.3 % by weight and supported thereon a catalytic substance of a constituent composition comprising (a) 1 mole of vanadium pentoxide, (b) 0.3 to 1.2 moles of molybdenum trioxide, (c) 0.005 to 0.05 moles of phosphorus pentoxide, (d) 0.03 to 0.2 moles of sodium oxide and (d) 0 to 0.05 moles of potassium oxide.

14 Claims, No Drawings

CATALYST FOR THE PREPARATION OF MALEIC ANHYDRIDE

This invention relates to a catalyst for the preparation of maleic anhydride by vapor phase catalytic oxidation of benzene with a molecular oxygen containing gas and, in particular, to a catalyst for the preparation of maleic anhydride by vapor phase catalytic oxidation of benzene which brings about a high yield and retains its high performance for a long period of time. More particularly, it relates to a process for the preparation of maleic anhydride in a high yield and stationarily for a long period of time by vapor phase catalytic oxidation of benzene by the aid of a catalyst comprising (a) vanadium pentoxide $V_2O_5$, (b) molybdenum trioxide $MoO_3$, (c) phosphorus pentoxide $P_2O_5$, (d) sodium oxide $Na_2O$ and, optionally, (e) potassium oxide $K_2O$ supported on a porous inert support of an alkali metal content of at most 0.3% by weight calculated as oxides.

For industrially advantageous production of maleic anhydride by vapor phase catalytic oxidation of benzene, it is an important factor that a catalyst used has a long catalytic life and gives a high yield of maleic anhydride. Various catalysts partly meeting such essential factor have hitherto been proposed, but none of them completely meets the essential factor. For instances, there are known, as disclosed in, e.g., U.S. Pat. Nos. 3,211,671 and 3,535,346 and West German Offenlegungsschrift No. P 1,965,401, a catalyst system comprising vanadium pentoxide $V_2O_5$, molybdenum trioxide $MoO_3$, phosphorus pentoxide $P_2O_5$, sodium oxide $Na_2O$ and cobalt trioxide $Co_2O_3$, a catalyst system comprising $V_2O_5$, $MoO_3$, $P_2O_5$, $Na_2O$ and silver oxide $Ag_2O$ and a catalyst system comprising $V_2O_5$, $MoO_3$, $P_2O_5$, $Na_2O$ and bismuth trioxide $Bi_2O_3$, and high yields of maleic anhydride by oxidation of benzene of a level of 94 to 100% by weight have been attained by employing a catalyst prepared by supporting such a catalyst system on a porous inert support. However, the known catalysts have a shortcoming that, in spite of their high level of initial yield, they have short catalytic lives and lose catalytic activity within a short period of time, for instance the optimum reaction temperature rises by about 30° C in about one year and the yield decreases by about 3 to 5% by weight.

A common feature of the known catalysts is that there are employed porous supports. In general porous supports are effective for fastening thereon catalytic substances and effective also for enlarging apparent surface areas to enhance the efficiency of contact with reaction gases. However, in the porous supports there is used a large amount of a binder for providing suitable porous structures or molding into desired shapes and, in addition, as the binder preferably used in usual are alkali metal containing materials. Also there have been used, as the porous supports, naturally occurring materials, e.g. pumice, containing alkali metal compounds, alkaline earth metal compounds and other various compounds in large amounts.

In study of elucidating the cause for the deterioration in activity of the known catalysts, we have ascertained that, when such an alkali metal containing support as mentioned above is used, some components of the support, especially alkali metal components migrate into the catalytically active substances supported on the surface of the support in the course of reaction run and have a significant influence on the activity of the catalyst to vapor phase catalytic oxidation of benzene. That is to say, it has been discovered that the migration of trace amounts of alkali metal components alters the optimum composition of catalytic substances and that the catalytic activity is deteriorated more acutely by migration of alkali metals than by migration of alkaline earth metals and other metals. Moreover, it also has been found out that, when there is employed a support containing large amounts of alkali metals, it is necessary to determine the composition of a finished catalyst with taking into consideration the migration of alkali metals to the surface of the finished catalyst and yet the alkali metal content of the catalytically active composition varies with lapse of time to affect significantly the catalytic activity.

Accordingly, an object of the present invention is to provide an improved catalyst for the preparation of maleic anhydride.

Another object of the present invention is to provide an industrially excellent catalyst for the preparation of maleic anhydride in a high yield which can retain a high activity for a long period of time of reaction run, using a support of a low alkali metal content.

A still another object of the present invention is to provide a process for the preparation of maleic anhydride in high yield stationarily for a long period of time by catalytic oxidation of benzene in vapor phase.

The catalyst in accordance with the present invention for the preparation of maleic anhydride by vapor phase catalytic oxidation of benzene comprising a porous inert support of an alkali metal content, calculated as oxides, of at most 0.3% by weight and a catalytic substance supported thereon comprising (a) 1 mole of vanadium pentoxide $V_2O_5$, (b) 0.3 to 1.2 moles of molybdenum trioxide $MoO_3$, (c) 0.005 to 0.05 moles of phosphorus pentoxide $P_2O_5$, (d) 0.03 to 0.2 moles of sodium oxide $Na_2O$ and (e) 0 to 0.05 moles of potassium oxide $K_2O$.

As the support for catalyst in accordance with the present invention there is employed alpha-alumina or silicon carbide. It is most essential that the alkali metal content in the support does not exceed 0.3% by weight, preferably 0.15% by weight in the form of oxide. That is to say, influence of the support on the activity of the finished catalyst increases with increase of the alkali metal content, though the influence can be eliminated by appropriate choice of the proportions of catalytic components so long as the alkali metal content is 0.3% by weight or less. The support to be employed is required to be refractory, highly heat conductive and highly porous. The porosity should be of an apparent porosity of 20 to 70, preferably of 30 to 60%. The surface area of the support should be of 0.01 to 1 m²/g as determined by Brunauer-Emmett-Teller method (hereinafter referred to as "BET method"), preferably of 0.02 to 0.5 m²/g. The total volume of pores of diameters of 1 micron or more, preferably 10 microns or more should amount to at least 80% of the total volume of pores of diameters not exceeding 100 microns, as determined by means of a mercury penetrating porosimeter. The support may be in the form of particles such as, pellets, spheres, blocks or flakes of average sizes of 2 to 12 mm, preferably of 3 to 9 mm.

The support having the aforesaid shape and properties is prepared in, e.g., the following procedure.

Silicon carbide self sintered support

A granular high purity silicon carbide of particle sizes of 50 to 200 mesh is added with an organic binder, such as polyacrylic acid, starch or carboxymethylcellulose, kneaded, molded and heated at 2,100° to 2,400° C to effect sintering of particles of silicon carbide by decomposition and recombination of portion of silicon carbide.

alpha-Alumina support

A granular high purity alpha-alumina of particle sizes of 50 to 200 mesh is added with a suitable amount of water, cellulosic material and 3 to 7% by weight, based on the weight of alpha-alumina, of a clayey material containing silica, gamma-alumina, calcium, magnesium and small amounts of alkali metals, kneaded, molded and calcined at 1,100° to 1,400° C. During calcination, water and cellulosic material burn out to give requisite properties and structures to the finished support, i.e. serve for controlling, e.g., pore diameter and pore volume and the clayey material combines particles of alpha-alumina.

The proportions of catalytic constituents in the catalytic substance in accordance with the present invention are: per mole of $V_2O_5$, 0.3 to 1.2, preferably 0.4 to 1.0 mole of $MoO_3$, 0.005 to 0.05, preferably 0.01 to 0.04 moles of $P_2O_5$, 0.03 to 0.2, preferably 0.04 to 0.15 moles of $Na_2O$ and 0 to 0.05 moles of $K_2O$. The integral constituents of the catalyst of the present invention are not always restricted to the oxides as described in this specification, which are mere illustration of the compositions of finished catalysts.

Starting materials for the preparation of the catalyst may be suitably selected from compounds containing each constituent element, for instance, in case of metallic constituents, ammonium salts, sulfates, nitrates, carbonates, phosphates, halides, hydroxide, oxides and organic acid salts thereof. Typical examples of such compounds are: ammonium metavanadate, vanadium oxide, vanadic acid, ammonium molybdate, molybdenum chloride, molybdenum trioxide, sodium hydroxide, sodium oxide, sodium chloride, sodium carbonate, sodium formate, sodium acetate, sodium propionate, sodium nitrate, sodium sulfate, potassium hydroxide, potassium oxide, potassium chloride, potassium carbonate, potassium formate, potassium acetate, potassium nitrate and potassium sulfate. As the source of phosphorus there may be used, e.g., phosphorus pentoxide, phosphorus pentachloride, phosphoric acid, ammonium phosphate, ammonium sodium hydrogen phosphate, hydrogen diammonium phosphate, trisodium phosphate, dihydrogen ammonium phosphate and dihydrogen sodium phosphate.

On preparation of a catalyst, starting compounds of a catalytic substance are added to an aqueous solution of, e.g., a hydrochloric acid, sulfuric acid or like inorganic acid or an oxalic acid or like organic acid to obtain a catalyst constituent solution. Though it is preferred to use the catalyst constituent solution in the form of an aqueous solution, it may be used in mixture with an organic solvent, such as dimethylformamide or dimethylsulfoxide. The catalyst constituents contained in the catalyst constituent solution are supported on a porous support as mentioned above by soaking the support in the solutions and evaporating the solution to dryness and the support is then calcined in an oxidative atmosphere as set forth hereinafter to obtain an active catalyst. Alternately, a preferred result may be obtained also by spraying the catalyst constituent solution on to an inert support which has previously been heated in a jacketed evapolating dish or rotary drum. In this spray method, a support is thoroughly stirred as the catalyst constituents to be uniformly supported with maintaining the temperature of the support at 150° to 300°, preferably 200° to 250° C. Concurrently with supporting, the volatile matters in the solution are evaporated and removed. The so treated support is then subjected to calcination in a stream of an oxidative gas, such as air, to obtain an activated catalyst. The calcination is carried out at a temperature of 300° to 600°, preferably 400° to 500° C for a time of 2 to 10, preferably 4 to 8 hours.

The amount of the catalytically active substance supported in the finished catalyst thus obtained (most of the constituents of the substance are detected in the form of oxides) is within the range of 3 to 15 g, preferably 7 to 12 g per 100 ml of support.

For the preparation of maleic anhydride by using the catalyst in accordance with the present invention, a steel or stainless steel reaction tube of an inner diameter of 15 to 35, preferably 20 to 30 mm is packed with the catalyst and immersed in a fused salt bath. A mixture of benzene and a molecular oxygen containing gas is passed through the catalyst bed in the tube to effect vapor phase oxidation of benzene. The fused salt bath is maintained at a temperature of 330° to 450°, preferably 350° to 420° C. As the molecular oxygen containing gas usually used is air, though there may be used gaseous oxygen diluted with an inert gas, such as gaseous nitrogen or gaseous carbon dioxide. The concentration of a raw gas supplied to a reaction zone may be, in case where air is employed as the molecular oxygen containing gas, 15 to 40 liters-air/g-benzene, preferably 20 to 30 liters-air/g-benzene. In case where there is employed a gaseous oxygen diluted with an inert gas as the oxidizing agent, the oxidation may be conducted under the similar conditions. The space velocity of the gaseous reaction mixture may be within the range of 1,500 to 4,000, preferably 2,000 to 3,000 hr $^{-1}$ (N.T.P.).

The catalyst in accordance with the present invention could retain high activity and selectivity as indicated by a high yield of maleic anhydride of 95 to 100% by weight over a long period of time of 1 year or more and it was unnecessary to elevate the salt bath temperature at all.

In the following EXAMPLES and CONTROLS, all yields were calculated by the following equation:

$$\text{Yield (\%)} = \frac{\text{weight of product}}{\text{weight of benzene}} \times 100$$

wherein benzene used as a starting raw material was calculated as 100% benzene.

EXAMPLE 1

In 1,500 ml of distilled water there was dissolved 272 g of oxalic acid, then added and dissolved therein in turn 230 g of ammonium metavanadate, 69.4 g of ammonium molybdate, 11.2 g of trisodium phosphate and 2.5 g of sodium nitrate, with stirring, to obtain a catalyst constituent solution. The solution was then sprayed on to 1.8 kg of a spherical self sintered silicon carbide support of an average diameter of 7 to 8 mm in an externally heated rotary drum while maintaining the support at a temperature of 200 to 250° C and the support thus treated was calcined at 450° C for 8 hours in stream of air to obtain a finished catalyst of the catalytic composition in molar ratio of: $V_2O_5:MoO_3:P_2O_5:Na_2O = 1:0.40:0.015:0.06$, and of a supported amount of 8 g/100 ml-support.

The silicon carbide support used was of a silicon carbide content of 98.7% by weight, contained as impurities 0.4% by weight of silica $SiO_2$, 0.3% by weight of alumina $Al_2O_3$, 0.2 % by weight of ferric oxide $Fe_2O_3$ and 0.09% by weight, in total, of $Na_2O$ and $K_2O$, and had an apparent porosity of 38% and a BET surface area of 0.05 $m^2/g$. The total volume of pores of diameters of at least 10 microns amounted to 95% of the total volume of pores of diameters of 100 microns or less, as determined by means of a mercury porosimeter (Winslow Porosimeter, Aminco).

A stainless steel reaction tube of an inner diameter of 25 mm, to be immersed in a fused salt bath, was packed with the catalyst thus obtained to form a catalyst bed of a height of 2.5 m, the fused salt bath temperature (hereinafter it will be referred, for short, as N.T.) was set at 370° C, and a gaseous raw material of a concentration of 25 l-air/g-benzene was introduced therein at a space velocity (hereinafter referred to as S.V.) of 2,500 $hr^{-1}$ to carry out oxidation reaction. In this reaction run maleic anhydride was obtained in a yield of 95% by weight, and the high yield was maintained during a long period continuous reaction run for 1 year without any necessity to elevate N.T.

EXAMPLE 2

The same procedure as in EXAMPLE 1, except that ammonium molybdate was used in an amount of 130 g and trisodium phosphate and sodium nitrate were replaced by 4.5 g of ammonium phosphate and 8.3 g of sodium carbonate, was repeated to obtain a finished catalyst of a catalytic constituent composition in molar ratio of $V_2O_5:MoO_3:P_2O_5:Na_2O = 1:0.75:0.02:0.08$ and a supported amount of 8 g/100 ml-support. Benzene was oxidized using the catalyst thus obtained in the same manner as in EXAMPLE 1 except that N.T. was set at 380° C to obtain maleic anhydride in a yield of 99% by weight. The yield was maintained during a long period continuous run for 1 year without any necessity of elevating N.T.

EXAMPLE 3

In the same procedure as in EXAMPLE 1 except that ammonium molybdate and trisodium phosphate were used in amounts of 156 g and 29.8 g, respectively, and sodium nitrate was omitted, there was obtained a finished catalyst of a catalytic composition in molar ratio of $V_2O_5:MoO_3:P_2O_5:Na_2O = 1:0.90:0.04:0.12$ and of a supported amount of 8 g/100 ml-support. Oxidation of benzene was carried out in the same manner as in EXAMPLE 1 except that N.T. was set at 390° C to obtain maleic anhydride in a yield of 96% by weight. The yield was maintained during a long period continuous run for 1 year without any necessity of elevating N.T.

CONTROL 1

A finished catalyst was prepared in the same procedure as in EXAMPLE 2 except that there was used, in place, the following support and oxidation of benzene was carried out under the same conditions as in EXAMPLE 2.

The support used was a spherical silicon carbide support of an average diameter of 7 to 8 mm consisting of 78% by weight of silicon carbide, 14.5% by weight of $SiO_2$, 3.9% by weight of $Al_2O_3$, 0.4% by weight of $Fe_2O_3$, 0.8% by weight of calcium oxide CaO, 0.4% by weight of magnesium oxide MgO and 2.2% by weight, in total, of $Na_2O$ and $K_2O$. The support was of an apparent porosity of 42% and of a BET surface area of 0.08 $m^2/g$, in which the total volume of pores of diameters of at least 10 microns amounted to about 95% of the total volume of pores of diameters of 100 microns or less.

In a continuous run, after 1 month N.T. was 390° C and the yield of maleic anhydride was 91% by weight, though after 3 months N.T. rose to 420° C and the yield decreased to 88% by weight. Then, the catalyst was withdrawn and subjected to determination of potassium and sodium in the surface catalytic substance and potassium in the support by X-ray fluorescence analysis, atomic absorption analysis and X-ray microanalizer to confirm that the concentrations of potassium and sodium in the catalytic substance increased while that of potassium in the support decreased remarkably.

CONTROLS 2 to 6

The catalysts as listed in the following Table 1 were prepared using as raw material compounds for preparation of catalysts ammonium metavanadate, ammonium molybdate, monoammonium phosphate, sodium nitrate and potassium nitrate and the same support and in the same procedure as in EXAMPLE 1. Oxidation of benzene was carried out using the catalysts in the same manner as in EXAMPLE 1. The optimum N.T. and yield of maleic anhydride after continuous run for 1 month in each reaction run were as indicated in the Table 1.

Table 1

| Control Nos. | Composition of Catalysts (molar ratio) | | | | | N.T. (° C) | Yield of maleic anhydride (weight %) |
|---|---|---|---|---|---|---|---|
| | $V_2O_5$ | $MoO_3$ | $P_2O_5$ | $Na_2O$ | $K_2O$ | | |
| 2 | 1 | 0.7 | 0.02 | 0.015 | 0 | 410 | 86 |
| 3 | 1 | 0.7 | 0.02 | 0.015 | 0.1 | 420 | 84 |
| 4 | 1 | 0.7 | 0.02 | 0.1 | 0.15 | 430 | 84 |
| 5 | 1 | 0.7 | 0.02 | 0.3 | 0 | 405 | 83 |
| 6 | 1 | 0.7 | 0.02 | 0.4 | 0.05 | 420 | 84 |

EXAMPLE 4

In 1,500 ml of distilled water there was dissolved 258 g of oxalic acid, then added and dissolved therein in turn 230 g of ammonium metavanadate, 139 g of ammonium molybdate, 22.4 g of trisodium phosphate, 3.5 g of sodium chloride and 2.6 g of potassium sulfate, with stirring, to obtain a catalyst constituent solution. The solution was then supported on an alpha-alumina support in the form of cylindrical pellets each of a diameter 6 mm and a height 6 mm by spraying on to 1.8 kg of the support maintained at 200° to 250° C in an externally heated rotary drum and calcined at 420° C for 6 hours in stream of air to obtain a finished catalyst of a catalytic constituent composition in molar ratio of $V_2O_5$:$MoO_3$:$P_2O_5$:$Na_2O$:$K_2O = 1:0.80:0.03:0.12:0.015$ and of a supported amount of 10 g catalytic substance/100 ml-support.

The alpha-alumina support used was such that contained 95.5% by weight of alumina and, as impurities and ingredients derived from a binder, 3.5% by weight of $SiO_2$, 0.2% by weight of $Fe_2O_3$, 0.2% by weight of CaO, 0.1% by weight of MgO and 0.15% by weight, in total, of $Na_2O$ and $K_2O$, had an apparent porosity of 55% and a BET surface area of about 0.07 $m^2/g$ and the total pore volume of pores of diameters of at least 10 microns amounted to 100% of the total pore volume of pores of diameters not exceeding 100 microns.

A stainless steel reaction tube of an inner diameter of 25 mm immersed in a fused salt bath was packed with the catalyst to form a catalyst bed of a height of 2 m and the N.T. was set at 375° C. Into the reaction tube there was introduced at a S.V. of 2,800 hr$^{-1}$ a raw material mixed gas of a benzene concentration of 25 l-air/g-benzene to carry out oxidation. During a continuous run for 6 months a yield of maleic anhydride of 95 to 96% by weight was maintained without any rise of N.T.

CONTROL 7

A catalyst was prepared in the same procedure as in EXAMPLE 4 except there was used another support and oxidation of benzene was carried out in the same manner as in EXAMPLE 4.

There was used 1.8 kg of a spherical alumina support of an average diameter of 5 to 6 mm consisting of 86.0% by weight of $Al_2O_3$, 12.0% by weight of $SiO_2$, 0.15% by weight of $Fe_2O_3$, 0.85% by weight of CaO, 0.05% by weight of MgO and 0.6% by weight, in total, of $Na_2O$ and $K_2O$. The apparent porosity of the support was 59%, the BET surface area was about 0.1 m$^2$/g, and the total volume of pores of diameters of at least 10 microns amounted about 95% of the total volume of pores of diameters not exceeding 100 microns.

In continuous run, the yield of maleic anhydride at a N.T. of 390° C was 93% by weight after 1 month, though the optimum N.T. rose to 425° C and the yield of maleic anhydride decreased to 88% by weight after 6 months. Then, the catalyst was withdrawn and subjected to analysis of potassium and sodium contained in the catalytic substance and potassium contained in the support to confirm that the contents of potassium and sodium in the catalytic substance increased while, on the other hand, potassium in the support decreased remarkably compared with the catalyst before use.

CONTROLS 8 to 12

The catalysts, as listed in the following Table 2, were prepared using as starting raw materials for catalysts ammonium metavanadate, ammonium molybdate, monoammonium phosphate, trisodium phosphate, sodium chloride and potassium carbonate and the same support as used in EXAMPLE 4 in the same manner as in EXAMPLE 4. Oxidation of benzene was carried out using the catalysts. The optimum N.T. and yield of maleic anhydride after continuous run for 1 month were as summarized in the following Table 2.

TABLE 2

| Control Nos. | Composition of catalyst (molar ratio) | | | | | N.T. (° C) | Yield of maleic anhydride (wt. %) |
|---|---|---|---|---|---|---|---|
| | $V_2O_5$ | $MoO_3$ | $P_2O_5$ | $Na_2O$ | $K_2O$ | | |
| 8 | 1 | 0.8 | 0.03 | 0.01 | 0 | 410 | 87 |
| 9 | 1 | 0.8 | 0.03 | 0.01 | 0.02 | 440 | 82 |
| 10 | 1 | 0.8 | 0.03 | 0.09 | 0.2 | 420 | 79 |
| 11 | 1 | 0.8 | 0.03 | 0.5 | 0.01 | 390 | 85 |
| 12 | 1 | 0.8 | 0.03 | 0.5 | 0.1 | 410 | 80 |

CONTROL 13

A catalyst was prepared in the same procedure as in EXAMPLE 2 except that there was used another support and oxidation of benzene was carried out in the same manner as in EXAMPLE 1. The support used was 2.3 kg of an irregular shaped fused alumina support of a representative size of 7 to 8 mm consisting of 99.8% by weight of alpha-alumina, 0.03% by weight of $SiO_2$, 0.04% by weight of $Fe_2O_3$ and 0.05% by weight, in total, of $Na_2O$ and $K_2O$. The apparent porosity of the support was 9% and the BET surface area was about less than 0.01 m$^2$/g, and the total volume of pores of diameters not exceeding 100 microns was very small. Maleic anhydride was obtained using this catalyst in a yield of 91% by weight at a N.T. of 410° C. In this catalyst, the catalytically active layer on the surface of the support is liable to be peeled off, so that, after 6 months of continuous run, the reaction tube became unusable because of an excessively high pressure drop therein attributable to the dusts of the catalyst.

What is claimed is:

1. A catalyst for the preparation of maleic anhydride by vapor phase catalytic oxidation of benzene with a molecular oxygen containing gas consisting of a porous inert support selected from the group consisting of silicon carbide and alpha alumina having an alkali metal content, calculated as oxide, of at most 0.3% by weight and supported thereon a catalytic substance of a constituent composition consisting of (a) 1 mole of vanadium pentoxide, (b) 0.3 to 1.2 moles of molybdenum trioxide, (c) 0.005 to 0.05 moles of phosphorus pentoxide, (d) 0.03 to 0.2 moles of sodium oxide and (e) 0 to 0.05 moles of potassium oxide.

2. A catalyst for the preparation of maleic anhydride by vapor phase catalytic oxidation of benzene with a molecular oxygen containing gas consisting of a porous inert support selected from the group consisting of silicon carbide and alpha alumina of which the alkali metal content, calculated as oxide, at most 0.3% by weight, the apparent porosity of 20 to 70%, the BET surface area is 0.01 to 1 m$^2$/g and the total volume of pores of diameters of at least 1 micron amounts to at least 80% of the total volume of pores of diameters not exceeding 100 microns, and supported thereon a catalytically active substance of a constituent composition consisting of (a) 1 mole of vanadium pentoxide, (b) 0.3 to 1.2 moles of molybdenum trioxide, (c) 0.005 to 0.05 moles of phosphorus pentoxide, (d) 0.02 to 0.2 moles of sodium oxide and (e) 0 to 0.05 moles of potassium oxide.

3. A catalyst for the preparation of maleic anhydride by vapor phase catalytic oxidation of benzene with a molecular oxygen containing gas consisting of a porous inert support selected from the group consisting of silicon carbide and alpha alumina having an alkali metal content, calculated as oxide, of at most 0.3% by weight and supported thereon a catalytically active substance of a constituent composition consisting of (a) 1 mole of vanadium pentoxide, (b) 0.4 to 1.0 mole of molybdenum trioxide, (c) 0.01 to 0.4 moles of phosphorus pentoxide, (d) 0.04 to 0.15 moles of sodium oxide and (e) 0 to 0.5 moles of potassium oxide.

4. A catalyst as defined in claim 1 in which the inert support is of an apparent porosity of 20 to 70% and of a BET surface area of 0.01 to 1 m$^2$/g.

5. A catalyst as defined in claim 1 in which the inert support is of an apparent porosity of 30 to 60% and of a BET surface area of 0.02 to 0.5 m$^2$/g.

6. A catalyst as defined in claim 4 in which the inert support is such that the total volume of pores of diameters of at least 1 micron amounts to at least 80% of the total volume of pores of diameters not exceeding 100 microns.

7. A catalyst as defined in claim 5 in which the inert support is such that the total volume of pores of diameters of at least 10 microns amounts to at least 80% of the total volume of pores of diameters not exceeding 100 microns.

8. A catalyst as defined in claim 1 in which the inert support is in the form of particles of an average diameter of 2 to 12 mm.

9. A catalyst as defined in claim 8 in which the inert support is a self sintered silicon carbide.

10. A catalyst as defined in claim 1 in which the inert support is of an alkali metal content, calculated as oxide, of at most 0.15% by weight.

11. A catalyst as defined in claim 1 in which the catalytically active substance is supported in an amount of 3 to 15 g/100 ml-support.

12. A catalyst as defined in claim 1 in which the catalytically active substance is supported in an amount of 7 to 12 g/100 ml-support.

13. A catalyst as defined in claim 3 in which the inert support has an alkali metal content, calculated as oxide, of at most 0.15% by weight, an apparent porosity of 20 to 70%, a BET surface area of 0.01 to 1 $m^2/g$ and a porous structure wherein the total volume of pores of diameters of at least 1 micron amounts to at least 80% of the total volume of pores of diameters not exceeding 100 microns.

14. A catalyst as defined in claim 3 in which the catalytically active substance is supported in an amount of 3 to 15 g/100 ml-support.

* * * * *